United States Patent
Bois (10) Patent No.: US 12,172,822 B2
(45) Date of Patent: Dec. 24, 2024

(54) ASSEMBLY DEFINING A CHAMBER FOR AN ACTIVE MATERIAL

(71) Applicant: AIRNOV, INC., New Castle, DE (US)

(72) Inventor: Dominique Bois, Montreuil aux Lions (FR)

(73) Assignee: AIRNOV, INC., New Castle, DE (US)

(*) Notice: Subject to any disclaimer, the term of this patent is extended or adjusted under 35 U.S.C. 154(b) by 107 days.

(21) Appl. No.: 17/758,244

(22) PCT Filed: Dec. 31, 2020

(86) PCT No.: PCT/EP2020/088073
§ 371 (c)(1),
(2) Date: Jun. 30, 2022

(87) PCT Pub. No.: WO2021/136829
PCT Pub. Date: Jul. 8, 2021

(65) Prior Publication Data
US 2023/0013817 A1    Jan. 19, 2023

(30) Foreign Application Priority Data
Jan. 3, 2020 (EP) .................................... 20150264

(51) Int. Cl.
*B65D 81/26* (2006.01)
*B65D 43/16* (2006.01)
(Continued)

(52) U.S. Cl.
CPC ........... *B65D 81/266* (2013.01); *B65D 43/16* (2013.01); *B65D 51/30* (2013.01); *A61B 2050/3004* (2016.02); *A61J 1/03* (2013.01)

(58) Field of Classification Search
CPC .... B65D 81/266; B65D 43/162; B65D 25/04; A61B 10/0096; A61J 1/03
(Continued)

(56) References Cited

U.S. PATENT DOCUMENTS 3,135,566 A * 6/1964 Frank ..................... G07D 9/004
206/0.82
4,923,059 A * 5/1990 Evers ............... B65D 85/10484
229/125.17
(Continued)

FOREIGN PATENT DOCUMENTS

| CN | 1493506 A | 5/2004 |
|---|---|---|
| JP | 3037574 U | 5/1997 |

(Continued)

OTHER PUBLICATIONS

International Search Report with Written Opinion of the International Searching Authority, dated Apr. 1, 2021, with respect to International Application No. PCT/EP2020/088073.
(Continued)

*Primary Examiner* — Ernesto A Grano
(74) *Attorney, Agent, or Firm* — Scott R. Cox (57) ABSTRACT

This assembly includes a tubular body and a cap attached to the tubular body to define a chamber for an active material. The tubular body includes a transverse wall and a peripheral wall and the cap includes a base wall and a side wall. The chamber is delimited by a part of the tubular body including the transverse wall and is closed by the cap. The side wall of the cap on its periphery includes a plurality of longitudinal features in relief which cooperate by mutual engagement with complementary longitudinal features in relief provided on the peripheral wall of the tubular body substantially parallel to its longitudinal axis ($X_2$).

20 Claims, 8 Drawing Sheets

(51) Int. Cl.
  *B65D 51/30* (2006.01)
  *A61B 50/30* (2016.01)
  *A61J 1/03* (2023.01)
(58) Field of Classification Search
  USPC ........................................................ 206/205
  See application file for complete search history.

(56) References Cited

U.S. PATENT DOCUMENTS

| | | | | |
|---|---|---|---|---|
| 5,114,003 | A * | 5/1992 | Jackisch | B65D 81/268 |
| | | | | 206/204 |
| 5,680,946 | A | 10/1997 | Cochran | |
| 5,736,616 | A | 4/1998 | Ching et al. | |
| 5,788,064 | A * | 8/1998 | Sacherer | B65D 53/00 |
| | | | | 220/849 |
| 6,571,942 | B2 * | 6/2003 | Riemenschneider | |
| | | | | B65D 81/266 |
| | | | | 206/204 |
| 10,526,128 | B2 * | 1/2020 | Schneider | B29C 45/44 |
| 10,737,848 | B2 * | 8/2020 | Philip | B65D 51/30 |
| 10,974,887 | B2 * | 4/2021 | Freedman | B65D 81/264 |
| 11,325,771 | B2 * | 5/2022 | Freedman | B65D 53/02 |
| 2009/0120931 | A1 * | 5/2009 | Murray | B65D 51/165 |
| | | | | 53/396 |
| 2010/0140116 | A1 * | 6/2010 | Stiene | B65D 81/266 |
| | | | | 206/459.1 |
| 2011/0127176 | A1 * | 6/2011 | Chang | B65D 81/266 |
| | | | | 206/204 |
| 2012/0193246 | A1 * | 8/2012 | Chang | B65D 51/245 |
| | | | | 206/204 |
| 2013/0213828 | A1 * | 8/2013 | Chatterjee | A61J 1/03 |
| | | | | 206/204 |
| 2013/0220844 | A1 * | 8/2013 | Logel | B65D 43/162 |
| | | | | 206/204 |
| 2013/0334074 | A1 * | 12/2013 | Wada | B65D 55/16 |
| | | | | 206/204 |
| 2015/0136618 | A1 * | 5/2015 | Patel | B65D 81/22 |
| | | | | 206/0.5 |
| 2016/0031627 | A1 | 2/2016 | Yeh | |
| 2018/0016081 | A1 | 1/2018 | Schneider | |
| 2019/0241345 | A1 | 8/2019 | Logel et al. | |

FOREIGN PATENT DOCUMENTS

| | | |
|---|---|---|
| JP | 2002 274575 A | 9/2002 |
| JP | 2014218272 A | 11/2014 |
| KR | 20-0270743 Y | 4/2002 |
| WO | 9851758 A1 | 11/1998 |
| WO | 9948963 A2 | 9/1999 |
| WO | 2017139446 A1 | 8/2017 |
| WO | 2017207962 A1 | 12/2017 |
| WO | 2018149778 A1 | 8/2018 |

OTHER PUBLICATIONS

International Preliminary Report on Patentability of the International Searching Authority, dated Jul. 5, 2022, with respect to International Application No. PCT/EP2020/088073.

English Translation of Official Action issued by Korean Patent Office dated Aug. 29, 2024 with respect to parallel Korean Patent Application No. 10-2022-7026890.

* cited by examiner

ASSEMBLY DEFINING A CHAMBER FOR AN ACTIVE MATERIAL

FIELD OF THE INVENTION

The present invention relates to an assembly comprising a tubular body and a cap configured to be attached to the tubular body so as to define a chamber in which gases and vapors can enter to interact with an active material received in the chamber. Such an assembly may be, in particular, a vial, a canister or a stopper, notably for the packaging of sensitive products such as food, nutraceutical products, pharmaceutical products or diagnostic products. The present invention also relates to a method for manufacturing such an assembly.

BACKGROUND OF THE INVENTION

In the packaging or medical device industry, it is known to create, in a container intended to receive sensitive products, a chamber filled with an active material, so that gases and vapors present in the container can enter the chamber and be adsorbed by the active material. Such a chamber filled with an active material may be provided, e.g., in a packaging for sensitive products such as food, nutraceutical products, pharmaceutical products or diagnostic products, or in a medical device, notably in an inhaler such as a DPI (Dry Powder Inhaler). WO 2016/116551 A1 discloses a container which forms an accommodating space for a packaged good, where the container body has a chamber for an active material delimited in a bottom part of the container body. More precisely, the chamber is closed by a moisture-permeable and/or gas-permeable cover, which is engaged behind a peripheral groove present on an internal face of the lateral wall of the container body.

In this arrangement, the cover is locked between the active material and the peripheral groove. Then, the volume of active material received in the chamber must correspond to the volume of the chamber and cannot be modulated. The locking of the cover between the active material and the peripheral groove also does not allow for a robust attachment of the cover relative to the container body. In addition, the presence of the peripheral groove on the internal face of the container body limits the production rate of the container body by injection molding, since the cooling phase must be long enough to avoid damage of the groove during release of the part.

It is these drawbacks that the invention is intended more particularly to remedy by proposing an assembly comprising a tubular body and a cap configured to be attached to the tubular body so as to define a chamber, which makes it possible to optimize the volume of the chamber according to a quantity of active material received in the tubular body, the manufacturing of the assembly being simple, easily automated, and allowing high production rates.

DISCLOSURE OF THE INVENTION

For this purpose, a subject of the invention is an assembly, such as a vial, a canister or a stopper, comprising a tubular body and a cap configured to be attached to the tubular body so as to define a chamber for an active material, the tubular body comprising a transverse wall and a peripheral wall, the cap comprising a base wall and a side wall, wherein the chamber is delimited by a part of the tubular body including the transverse wall and is closed by the cap, wherein the side wall of the cap comprises on its periphery a plurality of longitudinal features in relief configured to cooperate by mutual engagement with complementary longitudinal features in relief provided on the peripheral wall of the tubular body substantially parallel to its longitudinal axis, wherein at least one longitudinal feature in relief of one among the cap and the tubular body has two flanks inclined with respect to a radial direction of the cap or tubular body passing through the feature in relief, wherein the cap is anchored relative to the tubular body by surface interference and, in the anchored configuration, both inclined flanks of the at least one longitudinal feature in relief of the one among the cap and the tubular body are in contact with a complementary longitudinal feature in relief of the other one among the cap and the tubular body.

Within the frame of the invention, the plurality of longitudinal features in relief of the cap are a plurality of recessed or projecting patterns with respect to a general surface of the side wall of the cap, such as longitudinal ribs or grooves. In the same way, the plurality of longitudinal features in relief of the tubular body are a plurality of projecting or recessed patterns with respect to a general surface of the peripheral wall of the tubular body, complementary to the recessed or projecting patterns of the cap, such as longitudinal grooves or ribs. The longitudinal features in relief of the cap may be provided either on an inner surface or on an outer surface of the side wall of the cap, the longitudinal features in relief of the tubular body then being provided either on an outer surface or on an inner surface of the peripheral wall of the tubular body. Throughout this text, a feature in relief is complementary to another feature in relief when it is configured to cooperate and interlock with the other feature, and the two features may have the same shape or different shapes. For example, two complementary features in relief may both have a V-shaped cross section, or they may include a first feature with a V-shaped cross section and a second feature with a rectangular cross section suitable for receiving and interlocking with the V-shaped first feature.

Thanks to the invention, the cap is attached securely to the tubular body, by surface interference between complementary features in relief, and with both inclined flanks of at least one feature in relief of one among the cap and the tubular body being in contact with a complementary longitudinal feature in relief of the other one among the cap and the tubular body. It is understood here that the complementary longitudinal feature in relief of the other one among the cap and the tubular body may either also have two inclined flanks, or may not have two inclined flanks.

Attachment by surface interference, or interference fit, corresponds to a deformation upon assembly of the cap and the tubular body, such that the outer diameter of the inner part among the cap and the tubular body, taken at an apex of the features in relief, is higher before assembly than once the cap is assembled with the tubular body. In a similar way, the inner diameter of the outer part among the cap and the tubular body, taken at a bottom of the features in relief, is lower before assembly of the cap and the tubular body than once they are assembled. In practice, the deformation is of the order of 0.5% to 3% in terms of circumference of the cap or the tubular body.

In the anchored configuration of the cap relative to the tubular body, the arrangement of the two inclined flanks of at least one feature in relief in contact with a complementary longitudinal feature in relief of the other part, provides not only a tightening in the radial direction of the assembly, but also a transversal tightening on the inclined flanks, which is substantially circumferential. This results in a stronger anchoring of the cap relative to the tubular body by surface interference.

Thanks to the invention, it is also possible to adjust the position of the cap along the longitudinal axis of the tubular body according to a quantity of active material present in the tubular body before the cap is mounted on the tubular body. In this way, the quantity of active material in the tubular body can be modulated to reach a desired level of regulation of the atmosphere within a container. It may be desired to adjust the quantity of active material present in the tubular body depending on the application. On the one hand, minimizing the quantity of active material allows for an increased storage volume for sensitive products; on the other hand, increasing the quantity of active material may allow for a longer shelf life. The quantity of active material may also be varied based on the properties, such as the moisture content, of the products to be stored in a container in which the atmosphere is regulated by means of the assembly of the invention.

In addition, thanks to the assembly of the cap and the tubular body by progressive engagement of the complementary features in relief, it is possible to apply a controlled force on the active material by means of the cap, making it possible to reach a desired level of compaction of the active material in the chamber. Thus, the quantity of active material can be higher than in conventional containers where a cover is locked behind a peripheral groove at a fixed position.

Moreover, with the assembly according to the invention, the particles of the active material can be compacted within the chamber and fully fill its volume. This is particularly advantageous because the bulk density of an active material, e.g. in the form of a powder, pellets or granules, is subjected to variations from one production to another. Then, when a defined weight of active material is to be guaranteed in an active container, the chamber for hosting the active material needs to be designed with an over-volume corresponding to the volume of the active material at its lowest bulk density. Consequently, in devices where the volume of the chamber cannot be adjusted, the chamber is usually not filled to its full volume, which results in a loss of storage volume in the container and in a loose distribution of the particles of the active material in the chamber, which may generate noise. On the contrary, the assembly according to the invention makes it possible to adjust the volume of the chamber to the effective volume of the active material, and thus receive a given weight of active material regardless of its volume.

The possibility to adjust the volume of the chamber for the active material is also advantageous in that it allows one and the same assembly to receive a great variety of active materials, including dehydrating agents (or desiccants) such as molecular sieves, silica gels, dehydrating clays; oxygen scavengers; odor absorbers; emitters of humidity or volatile olfactory organic compounds; or a mixture thereof. The assembly of the invention is also very versatile with respect to the physical form of the active material which may be, e.g., in the form of a powder, pellets, granules, tablets, or a mixture thereof.

The presence of longitudinal features in relief instead of a peripheral groove also makes it possible to obtain the cap and the tubular body easily by injection molding, the risks of damage during release of the parts being low because the longitudinal features in relief are obtained without molding undercuts. The filling of the tubular body with an active material, and the assembly of the cap and the tubular body, can also be totally automated, thus allowing high production rates.

According to one embodiment, a plurality of longitudinal features in relief of one part among the cap and the tubular body, distributed circumferentially over the periphery of the part, have two flanks inclined with respect to a radial direction of the cap or tubular body passing through the considered feature in relief and, in the anchored configuration of the cap relative to the tubular body by surface interference, both inclined flanks of each longitudinal feature in relief having inclined flanks are in contact with a complementary longitudinal feature in relief of the other part among the cap and the tubular body. In this embodiment, since a plurality of features in relief of one part, distributed circumferentially, have inclined flanks and are in contact with complementary features in relief of the other part in the anchored configuration, the resulting transversal tightening on the inclined flanks is distributed over the periphery of the assembly. This contributes to a strong anchoring of the cap relative to the tubular body over the entire periphery of the assembly.

According to one embodiment, at least one longitudinal feature in relief of the cap has two flanks inclined with respect to a radial direction of the cap passing through the feature in relief, whereas at least one longitudinal feature in relief of the tubular body has two flanks inclined with respect to a radial direction of the tubular body passing through the feature in relief, and, in the anchored configuration of the cap relative to the tubular body by surface interference, the two inclined flanks of the at least one longitudinal feature in relief of the cap are in contact with the two inclined flanks of the at least one longitudinal feature in relief of the tubular body. In this embodiment, there are at least two complementary features in relief, including one on the cap and one on the tubular body, each having two inclined flanks and, in the anchored configuration of the cap relative to the tubular body, the two complementary features in relief having inclined flanks are mutually engaged and the inclined flanks are in contact by pairs. In this case, the inclination of the cooperating flanks relative to the radial direction of the assembly ensures a tightening over a larger surface of the complementary features compared to, e.g., ribs and grooves of rectangular cross section with side walls parallel to the radial direction. This results in a stronger anchoring of the cap relative to the tubular body by surface interference.

According to one embodiment, a plurality of longitudinal features in relief of the cap, distributed circumferentially over the periphery of the cap, have two flanks inclined with respect to a radial direction of the cap passing through the considered feature in relief, whereas a plurality of longitudinal features in relief of the tubular body, distributed circumferentially over the periphery of the tubular body, have two flanks inclined with respect to a radial direction of the tubular body passing through the considered feature in relief, and, in the anchored configuration of the cap relative to the tubular body by surface interference, longitudinal features in relief of the cap having inclined flanks are engaged with complementary features in relief of the tubular body also having inclined flanks, such that the inclined flanks are in contact by pairs. This embodiment combines the advantages of the above embodiments, i.e., thanks to the circumferential distribution of the features in relief having inclined flanks, the resulting transversal tightening on the inclined flanks, which is substantially circumferential, is distributed over the periphery of the assembly; and, for each pair of complementary longitudinal features in mutual engagement both having inclined flanks, the inclination of the cooperating flanks relative to the radial direction of the assembly ensures a tightening over a larger surface of the complementary features. This contributes to a strong anchoring of the cap relative to the tubular body over the entire periphery of the assembly.

According to one embodiment, each longitudinal feature in relief of the cap has two flanks inclined with respect to a radial direction of the cap passing through the considered feature in relief, whereas each longitudinal feature in relief of the tubular body has two flanks inclined with respect to a radial direction of the tubular body passing through the considered feature in relief, and, in the anchored configuration of the cap relative to the tubular body by surface interference, each longitudinal feature in relief of the cap is engaged with a complementary feature in relief of the tubular body, such that the inclined flanks are in contact by pairs.

In one embodiment, in a section perpendicular to the longitudinal axis of the assembly, the inclined flanks of the features in relief of the cap having inclined flanks follow a homothetic profile of the inclined flanks of the features in relief of the tubular body having inclined flanks, according to the two different diameters of the cap and the tubular body. Then, the cap and the tubular body have a same pattern of inclined surfaces. Thanks to the complementary shapes, the contact pressure occurs not only in the radial direction of the assembly, but also on the inclined flanks perpendicularly to the inclined flanks, i.e. substantially circumferentially.

According to one embodiment, the longitudinal features in relief of the tubular body, respectively the longitudinal features in relief of the cap, are contiguous to one another on the periphery of the tubular body, respectively on the periphery of the cap. According to one feature, the longitudinal features in relief of the tubular body, respectively the longitudinal features in relief of the cap, form at least one striated surface on the periphery of the tubular body, respectively on the periphery of the cap. In particular, the cap and the tubular body may each comprise several striated surfaces distinct from one another and distributed around their periphery.

According to one embodiment, the cap comprises on its periphery a plurality of longitudinal ribs, each longitudinal rib having a rounded or chamfered end portion at each end of the longitudinal rib which is configured to interact first with a complementary longitudinal groove of the tubular body upon mutual engagement of the cap and the tubular body. Such rounded or chamfered end portions of the ribs make it possible to initiate easily the engagement of the longitudinal ribs of the cap with the longitudinal grooves of the tubular body, without having to precisely align the patterns. According to one feature, each rounded or chamfered end portion of a longitudinal rib has a chamfer angle of between 5° and 30° with respect to the side wall of the cap.

According to one embodiment, the length over which the longitudinal features in relief cooperate by mutual engagement is higher than 1/10 of the diameter of the tubular body, preferably higher than 1/6 of the diameter of the tubular body. The diameter of the tubular body which is considered for this evaluation is the diameter of the surface of the peripheral wall which comprises the longitudinal features in relief, which may be the inner surface or the outer surface of the peripheral wall depending on the application, taken at that end of the longitudinal features in relief engaged with those of the cap which is furthest from the transverse wall of the tubular body. Such a length of interaction between the features in relief ensures a strong attachment of the cap relative to the tubular body.

According to one embodiment, the successive longitudinal features in relief of the cap are distributed in the circumferential direction of the side wall with an angular pitch between two successive features in relief of less than 3°, preferably of the order of 2°. It is noted that, due to the complementary shape of the features in relief of the tubular body, the angular pitch between the features in relief of the tubular body is the same as that between the features in relief of the cap. Such an angular pitch of the successive features in relief on the cap and the tubular body provides a number of the complementary features in relief which ensures that the cap is properly anchored relative to the tubular body by surface interference. In particular, the higher the number of features in relief, the higher the tightening of the cap with respect to the tubular body.

According to one feature, the cap comprises on its periphery a plurality of longitudinal ribs each having a V-shaped cross section comprising an apex and two flanks, where each flank extends from the apex and is inclined with respect to a radial direction of the cap passing through the apex. According to one feature, the tubular body comprises on its periphery a plurality of longitudinal grooves each having a V-shaped cross section comprising a bottom and two flanks, where each flank extends from the bottom and is inclined with respect to a radial direction of the tubular body passing through the bottom. According to one embodiment, the angle at the apex of each longitudinal rib of the cap may be the same as the angle at the bottom of each longitudinal groove of the tubular body. According to another embodiment, the angle at the apex of each longitudinal rib of the cap may be higher than the angle at the bottom of each longitudinal groove of the tubular body, e.g. with an angle difference of the order of 2° to 10°. It may be interesting to have ribs of the cap with a slightly higher top angle, i.e. slightly more open than the grooves the tubular body, to promote the contact on the inclined flanks and enhance radial interference.

In one embodiment, the two flanks of each longitudinal rib of the cap are inclined relative to each other at an angle of between 70° and 90°, preferably of the order of 80°. According to one feature, each longitudinal rib of the cap has a peak-to-valley height higher than 0.2 mm, preferably higher than 0.3 mm. Of course, due to their complementary shape, the features in relief of the tubular body also have similar ranges for their top angle and peak-to-valley height.

According to one feature, the two flanks of each longitudinal rib of the cap are inclined at a same angle on both sides of the radial direction passing through the apex, i.e. the radial direction passing through the apex is the bisector of the angle at the apex of each longitudinal rib, and it is the same for the two flanks of each longitudinal groove of the tubular body. According to one embodiment, the angle at the apex of each longitudinal rib of the cap, respectively the angle at the bottom of each longitudinal groove of the tubular body, is between 70° and 90°, preferably of the order of 80°. According to one embodiment, for each longitudinal rib of the cap, the inclination angle of each flank relative to a radial direction passing through the apex of the rib is between 35° and 45°, preferably of the order of 40°. According to one embodiment, for each longitudinal groove of the tubular body, the inclination angle of each flank relative to a radial direction passing through the bottom of the groove is between 35° and 45°, preferably of the order of 40°.

According to one feature, the bottom of each longitudinal groove of the tubular body has a pointed shape, whereas the apex of each longitudinal rib of the cap has a rounded shape. In this way, for each pair of complementary longitudinal rib and groove in mutual engagement, a gap, i.e. an empty space, is left between the apex of the rib and the bottom of the groove. This gap allows a deformation of the longitudinal ribs of the cap and the longitudinal grooves of the tubular body in mutual engagement, so that the contact surface, and thus the tightening, between the cap and the tubular body is maximized. The curvature (or truncation, e.g. to form a trapezoidal rather than a triangular profile in cross section) at the apex of each longitudinal rib of the cap also improves contact on the inclined flanks by avoiding a contact at a pointed end of the rib which would lead to a radial (centripetal) tightening force and would be less effective. It is noted that, when the longitudinal features in relief of the cap, respectively the longitudinal features in relief of the tubular body, are contiguous, a bottom is formed between two adjacent ribs of the cap, whereas an apex is formed between two adjacent grooves of the tubular body. In this case, the same configuration, with a pointed shape of each bottom of the cap and a rounded shape of each apex of the tubular body, is also advantageously implemented so that a gap is present between each pair of facing apex and bottom.

According to one feature, when the longitudinal features in relief of the tubular body are located on the inner surface of its peripheral wall, they extend until the transverse wall of the tubular body, i.e. they are connected to the transverse wall of the tubular body. Thanks to this arrangement, the presence of undercuts on the tubular body is avoided, and the tubular body can be manufactured by injection molding in an efficient way, without damage of the part when it is released from the mold.

According to one embodiment, the side wall of the cap and the peripheral wall of the tubular body each have a draft angle, the absolute value of the difference between the draft angle of the side wall of the cap and the draft angle of the peripheral wall of the tubular body being less than 3°, preferably less than 1°. This ensures that the complementary surfaces of the features in relief of the cap and the tubular body are substantially parallel, thus enhancing the tightening of the cap relative to the tubular body. According to one embodiment, the values of the draft angles for the side wall of the cap and the peripheral wall of the tubular body are selected to be between 0.5° and 1°, preferably of the order of 0.5°.

According to one embodiment, the tubular body comprises abutment means, such as abutment ribs, defining a position of maximum engagement of the cap relative to the tubular body toward the transverse wall. It is noted that, within the frame of the invention, the cap does not systematically rest on the abutment means. In particular, as mentioned above, the position of the cap can be adjusted according to the quantity of active material received in the tubular body.

According to one embodiment, the base wall of the cap comprises at least one hole covered with a gas-permeable protective sheet. The gas-permeable protective sheet makes it possible to avoid escape of the active material out of the chamber through the hole(s) of the cap. In one embodiment, the gas-permeable protective sheet is a cardboard. In another embodiment, the gas-permeable protective sheet is a porous membrane closing the hole. In the latter case, the membrane is advantageously secured to a wall of the cap around the periphery of the hole(s), e.g. by heat-sealing, ultrasonic welding, overmolding, etc.

In one embodiment of the invention, the assembly is a vial for the storage of products, in particular sensitive products, the tubular body being a container inside which the cap delimits two compartments located on both sides of the cap, including the chamber for an active material on one side and a fillable tank for the storage of products on the other side. According to one feature, the side wall of the cap is a tubular wall having an open end on the opposite side from the base wall, the cap being positioned in the container such that the open end faces away from the transverse wall of the container. In this way, the inner volume of the cap is part of the fillable tank and products can be stored therein.

In another embodiment of the invention, the tubular body and the cap form together a canister delimiting the chamber for an active material, the canister being intended to be dropped in a container intended to receive sensitive products and regulate the atmosphere inside the container. Such a canister advantageously has an adjustable volume.

In another embodiment of the invention, the tubular body and the cap are part of a stopper inside which they delimit the chamber for an active material, the stopper being configured to close a container intended to receive sensitive products and regulate the atmosphere inside the container.

According to one embodiment, the chamber is filled with an active material, in particular in a powder or granular state, which may be any type of active material. Within the meaning of the invention, an active material is a material capable of regulating the atmosphere in a container, especially in a container intended to receive sensitive products. In particular, the active material may belong to a group of: humidity absorbers; oxygen scavengers; odor absorbers; and/or emitters of humidity or volatile olfactory organic compounds. Optionally, the active material may be capable of releasing gaseous substances such as moisture or perfume. Such properties can for example be useful for applications where sensitive products require a certain humidity level. Such products are, for example, powders, especially for generating aerosols, gelatin capsules, herbal medicine, gels and creams including cosmetics, and food products.

Examples of suitable dehydrating agents include, without limitation, silica gels, dehydrating clays, activated alumina, calcium oxide, barium oxide, natural or synthetic zeolites, molecular or similar sieves, or deliquescent salts such as magnesium sulfide, calcium chloride, aluminum chloride, lithium chloride, calcium bromide, zinc chloride or the like. Preferably, the dehydrating agent is a molecular sieve and/or a silica gel.

Examples of suitable oxygen collecting agents include, without limitation, metal powders having a reducing capacity, in particular iron, zinc, tin powders, metal oxides still having the ability to oxidize, in particular ferrous oxide, as well as compounds of iron such as carbides, carbonyls, hydroxides, used alone or in the presence of an activator such as hydroxides, carbonates, sulfites, thiosulfates, phosphates, organic acid salts, or hydrogen salts of alkaline metals or alkaline earth metals, activated carbon, activated alumina or activated clays. Other agents for collecting oxygen can also be chosen from specific reactive polymers such as those described for example in the patent documents U.S. Pat. No. 5,736,616 A, WO 99/48963 A2, WO 98/51758 A1 and WO 2018/149778 A1.

According to one feature, each one of the cap and the tubular body is made of a suitable polymer material. Examples of suitable polymer materials include, without limitation, radical or linear high- and low-density polyethylene, copolymers of ethylene such as for example ethylene vinyl acetates, ethylene ethyl acrylates, ethylene butyl acrylates, ethylene maleic anhydrides, ethylene alpha olefins, regardless of the methods of polymerization or modification by grafting, polypropylene, polybutylene, polyisobutylene.

Polyolefins are advantageously selected to make the cap and the tubular body, for cost reasons and because they are easy to use. However, other polymer materials can also be considered, such as polyvinyl chloride, copolymers of vinyl chloride, polyvinylidene chlorides, polystyrenes, copolymers of styrene, derivatives of cellulose, polyamides, polycarbonates, polyoxymethylenes, polyethylene terephthalates, polybutylene terephthalates, copolyesters, polyphenylene oxides, polymethyl methacrylates, copolymers of acrylate, fluoride polymers, polyimides, polyurethanes, etc.

Combinations of these polymers can be used, if desired. The polymers used to produce the cap and the tubular body can also contain one or more additives such as fibers, expanding agents, additives such as stabilizers and colorants, sliding agents, demolding agents, adhesion agents or reinforced catching agents and/or any others according to the requirements of usage.

According to one embodiment, the cap and/or the tubular body can be obtained from injectable thermoplastic materials made in such a way that they act themselves as atmosphere regulators, e.g. capable of absorbing various different pollutants such as humidity, oxygen, odor and other possible pollutants. In this case, the thermoplastic materials constituting the cap and/or the tubular body are themselves formulated with additives belonging to a group of: humidity absorbers; oxygen scavengers; odor absorbers; and/or emitters of humidity or volatile olfactory organic compounds. Examples of suitable additives include the dehydrating agents and oxygen collecting agents listed above. It is noted that the thermoplastic materials formulated with such additives exhibit a lower elasticity. However, a lower elasticity is compatible with the assembly according to the invention, where the cap is anchored relative to the tubular body by surface interference between the complementary features in relief. In particular, such an assembly process does not require the same degree of resilience of the parts as is required, e.g., for a locking behind a peripheral groove.

According to one embodiment, the Young's modulus of the constitutive material of the cap is less than or equal to the Young's modulus of the constitutive material of the tubular body. When the constitutive materials of the cap and the body have substantially the same Young's modulus, the tightening of the cap with respect to the tubular body may be enhanced, through the establishment of a balanced interaction between the longitudinal features in relief of the two parts. The selection of a material having a lower Young's modulus for the cap can allow for an easier engagement of the cap relative to the tubular body.

Another subject of the invention is a method for manufacturing an assembly as described above, comprising steps in which:
- a part of the tubular body including the transverse wall is filled with an active material;
- the longitudinal features in relief of the cap are engaged with the complementary longitudinal features in relief of the tubular body until the base wall of the cap abuts the active material received in the tubular body.

According to one embodiment, the cap is engaged relative to the tubular body by means of an actuator, until a predetermined force applied on the cap by the actuator is reached, respectively until a predetermined stroke of the actuator is reached, wherein said predetermined force, respectively said predetermined stroke, corresponds to a predefined level of compaction of the active material in the chamber.

In an advantageous manner, the manufacturing of the assembly according to the invention can be totally automated. In particular, the step of assembling the cap and the tubular body can be implemented by an actuator which has been set to apply the predetermined force, or to run over the predetermined stroke, thus allowing to reach a desired predefined level of compaction of the active material in the chamber.

BRIEF DESCRIPTION OF THE DRAWINGS

Features and advantages of the invention will become apparent from the following description of several embodiments of an assembly and a method according to the invention, this description being given merely by way of example and with reference to the appended drawings in which.

ILLUSTRATIVE EMBODIMENTS OF THE INVENTION

In the first embodiment shown in FIGS. 1 to 11, the assembly 1 according to the invention is a vial for the storage of sensitive products, such as diagnostic test strips, or nutraceutical or pharmaceutical products e.g. in the form of pills, lozenges or tablets, notably effervescent tablets. The assembly 1 comprises a moisture-proof container, including a tubular body 2 and a lid 3 for hermetically closing the tubular body 2. The tubular body 2 and the lid 3 are connected to each other via a hinge, such as a film hinge. The assembly 1 also comprises a cap 4, attached inside the tubular body 2, which delimits two compartments located on both sides of the cap 4, including a chamber 6 for an active material on one side and a fillable tank 7 for sensitive products on the other side.

By way of a non-limiting example, the sensitive products received in the tank 7 may be diagnostic test strips 10, or nutraceutical or pharmaceutical products e.g. in the form of pills, lozenges or tablets, whereas the active material 5 received in the chamber 6 may be a dehydrating agent (or desiccant) in a powder or granular form, e.g. selected from molecular sieves, silica gels and/or dehydrating clays. As visible in FIGS. 1 and 10, the tubular body 2 has a circular cross section, and comprises a transverse wall 20, a peripheral wall 22 and an open end 23 on the opposite side from the transverse wall 20, which is configured to be closed by the lid 3. The cap 4 also has a tubular shape with a circular cross section, and comprises a base wall 40, a side wall 42, and an open end 43 on the opposite side from the base wall 40.

Figure 1:
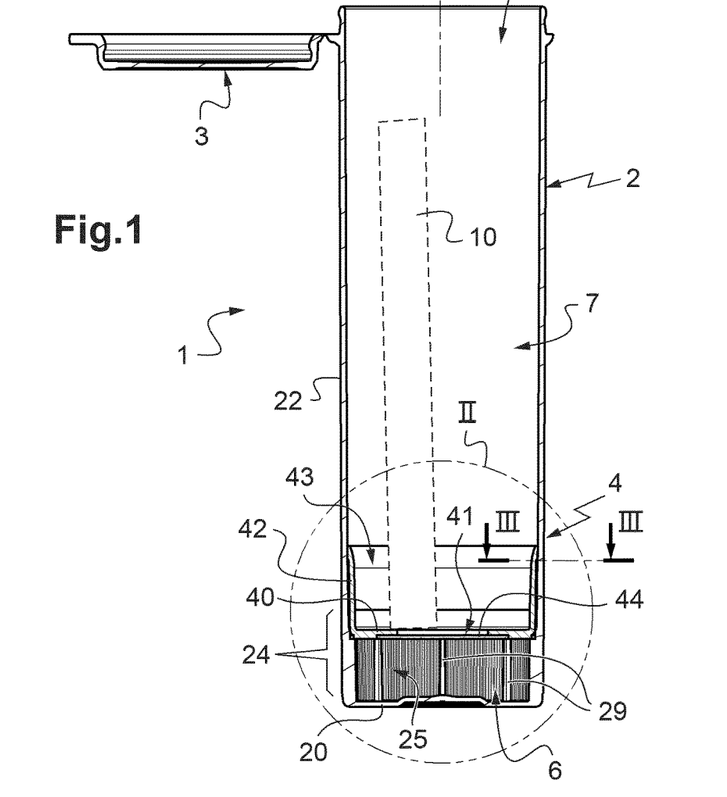
FIG. 1 is a longitudinal section of an assembly according to a first embodiment of the invention being a vial for the storage of products, which comprises a container including a tubular body inside which a cap delimits two compartments located on both sides of the cap, i.e. the chamber for an active material on one side and a Tillable tank on the other side.

The chamber 6 for the active material 5 is delimited by a bottom part 24 of the tubular body 2 including the transverse wall 20, and it is closed by the cap 4. Advantageously, the cap 4 is positioned in the tubular body 2 such that its open end 43 faces away from the transverse wall 20. In this way, the inner volume of the cap 4 is part of the fillable tank 7 and sensitive products such as diagnostic test strips 10 can be stored therein, as shown in FIG. 1. The base wall 40 of the cap 4 comprises a central hole 41, which is covered with a gas-permeable cardboard 44 to avoid escape of the active material 5 out of the chamber 6 through the hole. As visible in FIG. 2, the cardboard 44 is advantageously retained in a recess of the base wall 40, in a position in which it closes the hole 41.

As best seen in FIGS. 3 to 11, for the attachment of the cap 4 relative to the tubular body 2, the side wall 42 of the cap 4 comprises on its outer periphery a plurality of longitudinal ribs 47 configured to cooperate by mutual engagement with complementary longitudinal grooves 27 provided on the inner surface of the peripheral wall 22 of the tubular body 2, in the vicinity of the bottom part 24. The longitudinal grooves 27 are substantially parallel to the longitudinal axis $X_2$ of the tubular body 2. In the assembled configuration shown in FIGS. 1 to 4, the longitudinal ribs 47 of the cap 4, which are engaged with the longitudinal grooves 27 of the tubular body 2, are also substantially parallel to the longitudinal axis $X_2$.

The longitudinal ribs 47 and the longitudinal grooves 27 are configured in such a way that, when the longitudinal ribs 47 of the cap 4 are engaged with the longitudinal grooves 27 of the tubular body 2, the cap 4 is anchored relative to the tubular body 2 by surface interference. More precisely, as shown in the cross section of FIGS. 3 and 4, each longitudinal rib 47 of the cap 4 has a V-shaped cross section comprising an apex 470 and two flanks 471, where each flank 471 extends from the apex 470 and is inclined with respect to a radial direction of the cap 4 passing through the apex 470. In a similar way, each longitudinal groove 27 of the tubular body 2 has a V-shaped cross section comprising a bottom 270 and two flanks 271, where each flank 271 extends from the bottom 270 and is inclined with respect to a radial direction of the tubular body 2 passing through the bottom 270. In this embodiment, the angle at the apex of each longitudinal rib 47 is substantially the same as the angle at the bottom of each longitudinal groove 27, denoted δ in the figures.

Figure 3:
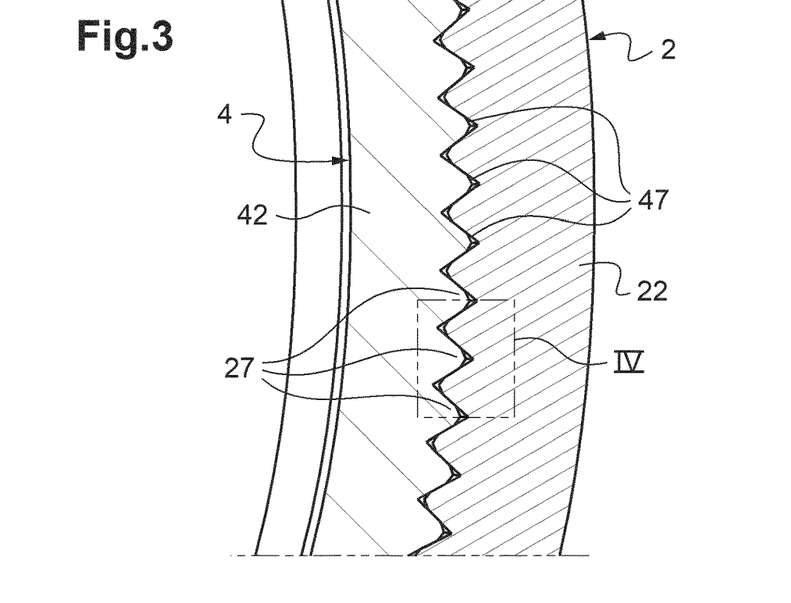
FIG. 3 is a cross section at larger scale along the line of FIG. 1.
Figure 4:
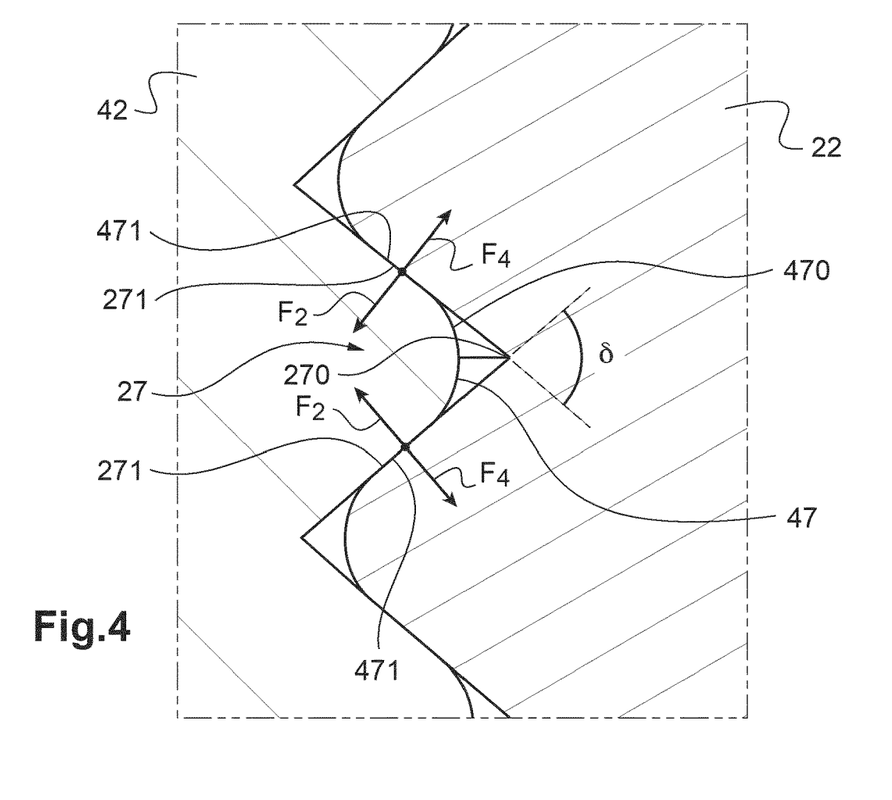
FIG. 4 is a view at larger scale of the detail IV of FIG. 3.
Figure 5:
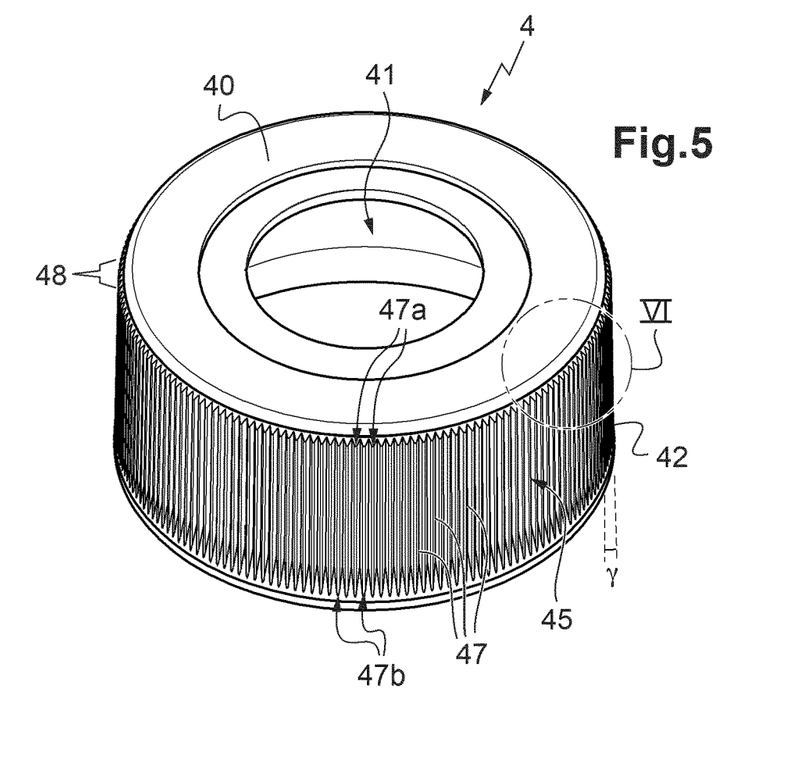
FIG. 5 is a perspective view of the cap of FIG. 1.

Preferably, as shown in the figures, the two flanks 471 of each longitudinal rib 47 are inclined at a same angle on both sides of the radial direction passing through the apex 470, i.e. the radial direction passing through the apex 470 is the bisector of the angle at the apex of each longitudinal rib 47, and it is the same for the two flanks 271 of each longitudinal groove 27. By way of a non-limiting example, in the illustrated embodiment, the angle δ at the apex of each longitudinal rib 47, respectively at the bottom of each longitudinal groove 27, is of the order of 80°. In the assembled configuration of the cap 4 in the tubular body 2, for each pair of complementary longitudinal rib 47 and groove 27 in mutual engagement, this corresponds to an inclination angle of each flank 471 or 271 of the order of 40° relative to a radial direction passing through the apex 470 and the bottom 270.

For each pair of complementary longitudinal rib 47 and groove 27 in mutual engagement, the inclination of the cooperating flanks 471 and 271 relative to the radial direction of the assembly ensures a tightening over a larger surface of the complementary features in relief 47 and 27 compared to, e.g., ribs and grooves of rectangular cross section with side walls parallel to the radial direction. For each pair of complementary longitudinal rib 47 and groove 27, the arrangement of the inclined flanks 471 and 271 in contact with each other by pairs provides not only a tightening in the radial direction of the assembly 1, but also a transversal tightening on the inclined flanks, which is substantially circumferential, as shown by the arrows $F_2$ and $F_4$ of FIG. 4 corresponding to the forces resulting from the contact between the inclined flanks. Thanks to the circumferential distribution of the longitudinal ribs 47 and grooves 27 having inclined flanks, the resulting transversal tightening on the inclined flanks is distributed over the periphery of the assembly 1. This results in a stronger anchoring of the cap 4 relative to the tubular body 2 by surface interference over the entire periphery of the assembly 1. In addition, as visible in the view at larger scale of FIG. 4, the bottom 270 of each longitudinal groove 27 of the tubular body 2 has a pointed shape, whereas the apex 470 of each longitudinal rib 47 of the cap 4 has a rounded shape. Thus, for each pair of complementary longitudinal rib 47 and groove 27 in mutual engagement, a gap is present between the apex 470 of the rib 47 and the bottom 270 of the groove 27. This empty space, combined with the elasticity of the constitutive polymer materials of the cap 4 and the tubular body 2, allows a deformation of both the longitudinal ribs 47 of the cap and the longitudinal grooves 27 of the tubular body so that the contact surface, and thus the tightening, is maximized between the cap 4 and the tubular body 2. In addition, the curvature at the apex of each longitudinal rib 47 of the cap 4 also improves contact between the inclined flanks 471 and 271, by avoiding a contact at a pointed end of the ribs 47 which would lead to a radial tightening force which would be less effective.

In this embodiment, the longitudinal ribs 47 on the cap 4 are contiguous to one another, and the longitudinal grooves 27 on the tubular body 2 are also contiguous to one another, so that a bottom is formed between each pair of adjacent ribs 47 of the cap and an apex is formed between each pair of adjacent grooves 27 of the tubular body. As shown in FIG. 4, the same configuration with a pointed shape of each bottom of the cap 4 and a rounded shape of each apex of the tubular body 2 is also implemented, so that a gap is present between each pair of apex and bottom. The dimensions of the gaps between each pair of apex and bottom of the assembly may advantageously be minimized to avoid passage of dust or particles of active material from the chamber 6 toward the fillable tank 7 intended to receive the sensitive products.

As visible in FIGS. 3 to 9, the longitudinal ribs 47 of the cap 4 are contiguous to one another and form a striated surface 45 all around the outer periphery of the cap. In the same way, as visible in FIGS. 8 and 9, the longitudinal grooves 27 of the tubular body 2 are contiguous to one another and form a striated surface 25 all around the inner periphery of the tubular body. The arrangement of the longitudinal ribs 47 and the longitudinal grooves 27 all around the periphery, together with the circular cross sections of the cap 4 and the tubular body 2, ensures that the relative engagement of the ribs and grooves is easily initiated, with a self-centering effect.

Figure 6:
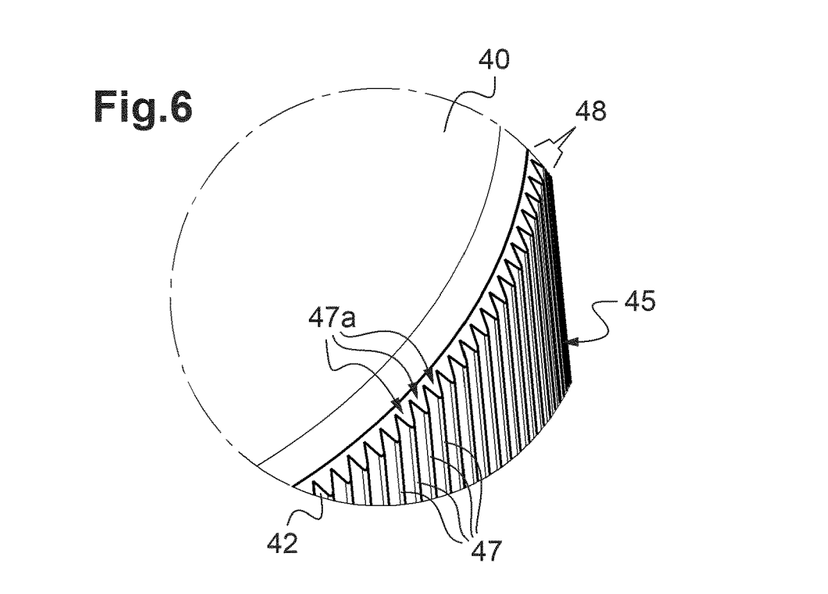
FIG. 6 is a view at larger scale of the detail VI of FIG. 5.
Figure 7:
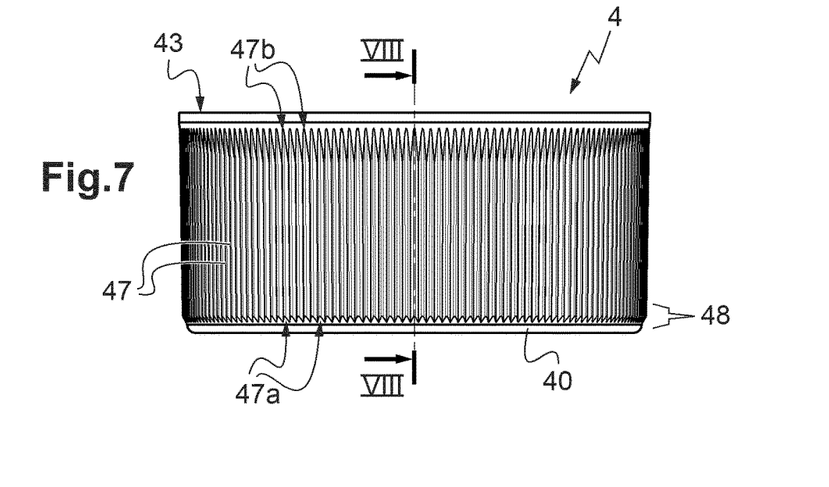
FIG. 7 is an elevation view of the cap of FIG. 1.
Figure 8:
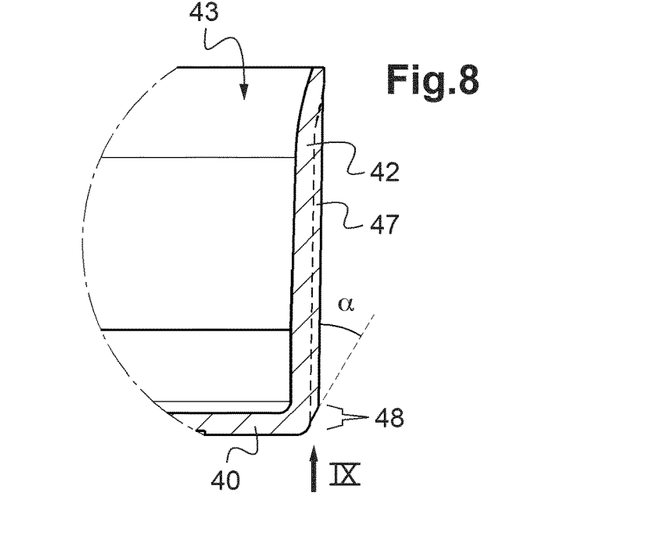
FIG. 8 is a cross section along the line VIII-VIII of FIG. 7.

As clearly visible in FIGS. 6 and 8, each longitudinal rib 47 of the cap 4 has a chamfered end portion 48 at its end 47a which is configured to interact first with a complementary longitudinal groove 27 of the tubular body 2 upon mutual engagement of the two parts. Such chamfered end portions 48 of the ribs 47 facilitate the engagement of the longitudinal ribs 47 of the cap with the longitudinal grooves 27 of the tubular body, without having to precisely align the patterns. In this embodiment, by way of a non-limiting example, each chamfered end portion 48 of a longitudinal rib 47 has a chamfer angle $\alpha$ of the order of 30° with respect to the side wall 42 of the cap. Of course, the other ends 47b of the ribs 47 may also exhibit a chamfered or rounded end portion if it is desired to insert the cap 4 in the tubular body with the ends 47b directed towards the transverse wall 20.

Figure 9:
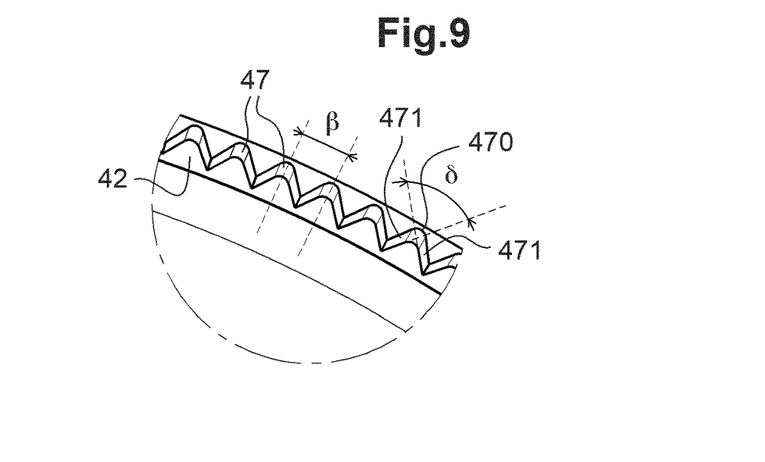
FIG. 9 is a view according to the arrow IX of FIG. 8.

As shown in FIG. 9, the successive longitudinal ribs 47 of the cap 4 are distributed in the circumferential direction of the side wall 42 with an angular pitch $\beta$ between two successive ribs of the order of 2°. Such a small pitch value facilitates the engagement of the longitudinal ribs 47 of the cap 4 with the longitudinal grooves 27 of the tubular body 2, without having to precisely pre-align the patterns angularly. FIG. 9 also shows the two flanks 471 of each longitudinal rib 47, which are inclined relative to each other at an angle $\delta$ of the order of 80° and connected at the apex 470, with a peak-to-valley height of the order of 0.30 mm. Of course, due to their complementary shape, the longitudinal grooves 27 of the tubular body 2 also have similar values of their angular pitch, top angle and peak-to-valley height. Such geometric characteristics of the ribs 47 and grooves 27 ensure that the cap 4 is properly anchored relative to the tubular body 2 by surface interference.

Figure 2:
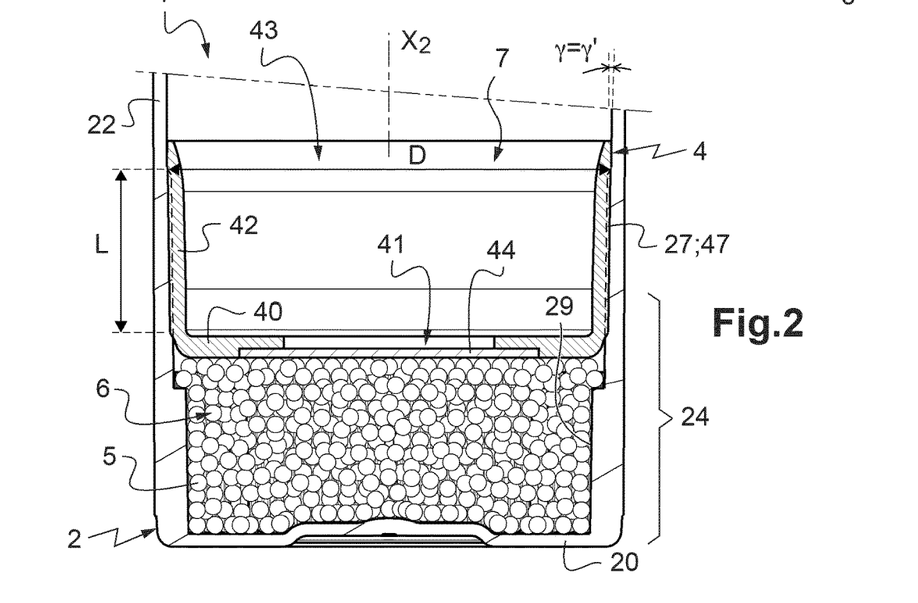
FIG. 2 is a view at larger scale of the detail II of FIG. 1, the chamber being filled with an active material.

Additionally, to ensure a strong attachment of the cap 4 relative to the tubular body 2, which may even be unremovable, the length L over which the longitudinal ribs 47 of the cap 4 cooperate with the longitudinal grooves 27 of the tubular body 2 is chosen to be higher than 1/10 of the diameter D of the tubular body, preferably higher than 1/6 of the diameter D of the tubular body. As shown in FIG. 2, the diameter D of the tubular body to be considered is the diameter of the inner surface of the peripheral wall 22 bearing the longitudinal grooves 27, taken at the end of the engagement of the grooves 27 with the ribs 47 which is furthest away from the transverse wall 20 of the tubular body.

Each one of the tubular body 2 and the cap 4 is advantageously obtained by injection molding of a thermoplastic material. High-density polyethylene (HDPE) and polypropylene are particularly suitable materials, because they provide a certain degree of rigidity to the parts, which may promote the establishment of a tightening interaction between the complementary surfaces of the ribs 47 and the grooves 27. A thermoplastic material formulated with an active material in its composition may also be used to make the tubular body 2 and/or the cap 4. The side wall 42 of the cap and the peripheral wall 22 of the tubular body may each have a draft angle, provided that the difference between the draft angle $\gamma$ of the side wall 42 of the cap and the draft angle $\gamma'$ of the peripheral wall 22 of the tubular body is low to ensure that the complementary surfaces of the ribs 47 and the grooves 27 are substantially parallel. By way of example, in the embodiment shown in the figures, the draft angles $\gamma$ and $\gamma'$ are chosen to be substantially equal to 0.5°.

Figure 10:
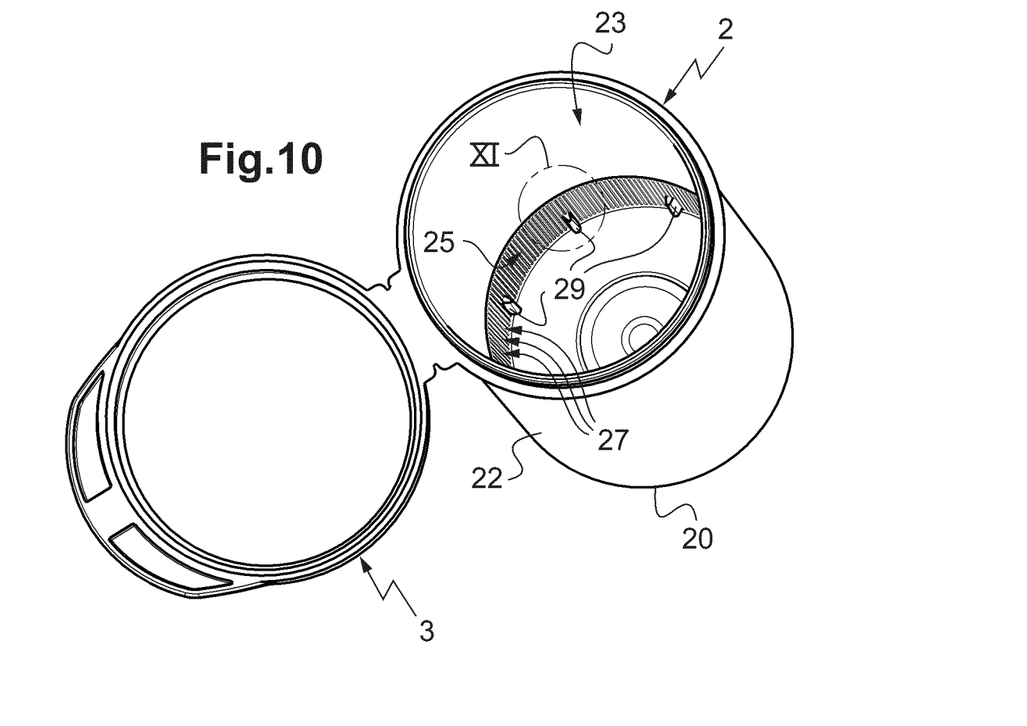
FIG. 10 is a perspective view of the tubular body of FIG. 1.
Figure 11:
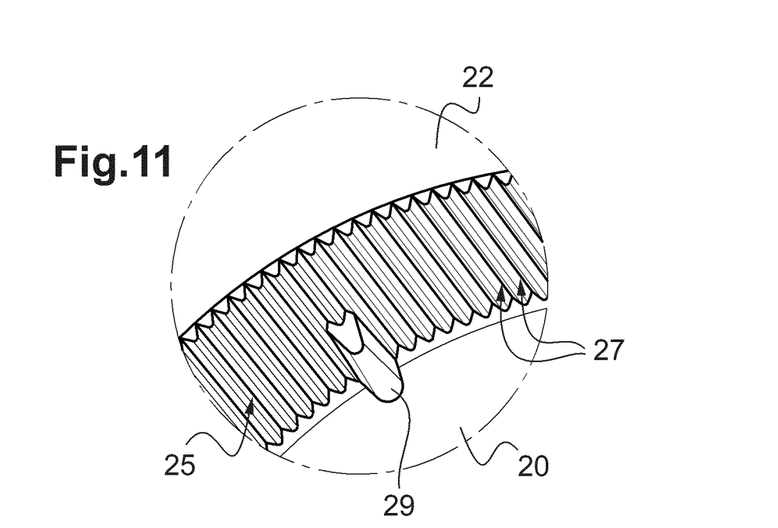
FIG. 11 is a view at larger scale of the detail XI of FIG. 10.

As visible in FIGS. 10 and 11, the longitudinal grooves 27 of the tubular body 2 extend down to the transverse wall 20 of the tubular body, i.e. their ends are connected to the transverse wall 20 of the tubular body in such a way as to limit the presence of undercuts on the tubular body and facilitate the molding of the tubular body. The tubular body 2 also comprises abutments 29, which define a position of maximum insertion of the cap 4 into the tubular body 2 in the direction of the transverse wall 20. Within the frame of the invention, the cap 4 does not systematically rest on the abutments 29 since its position can be adjusted according to the quantity of active material 5 received in the tubular body 2. In other embodiments of a vial for the storage of sensitive products according to the invention, the abutments 29 may be omitted.

In particular, FIG. 2 shows an arrangement where the volume of active material 5 is higher than the volume of the chamber 6 when the cap 4 abuts on the abutments 29. Thanks to the assembly of the cap 4 and the tubular body 2 by progressive engagement of the ribs 47 and grooves 27, it is possible to apply a controlled force on the active material 5 by means of the cap 4, making it possible to compact the active material 5 to a certain level in the chamber 6. A method for manufacturing the assembly 1 as described above may comprise successively a step of filling the tubular body 2 with an active material 5; then, a step of engaging the longitudinal ribs 47 of the cap 4 with the complementary longitudinal grooves 27 of the tubular body 2, until the base wall 40 of the cap 4 abuts the active material 5 received in the tubular body. In an advantageous manner, the step of assembling the cap 4 and the tubular body 2 can be totally automated and may be implemented by means of an actuator, such as a pneumatic, hydraulic or electric actuator, which is set to apply a predetermined force, or to run over a predetermined stroke, corresponding to a desired level of compaction of the active material 5 in the chamber 6.

Figure 12:
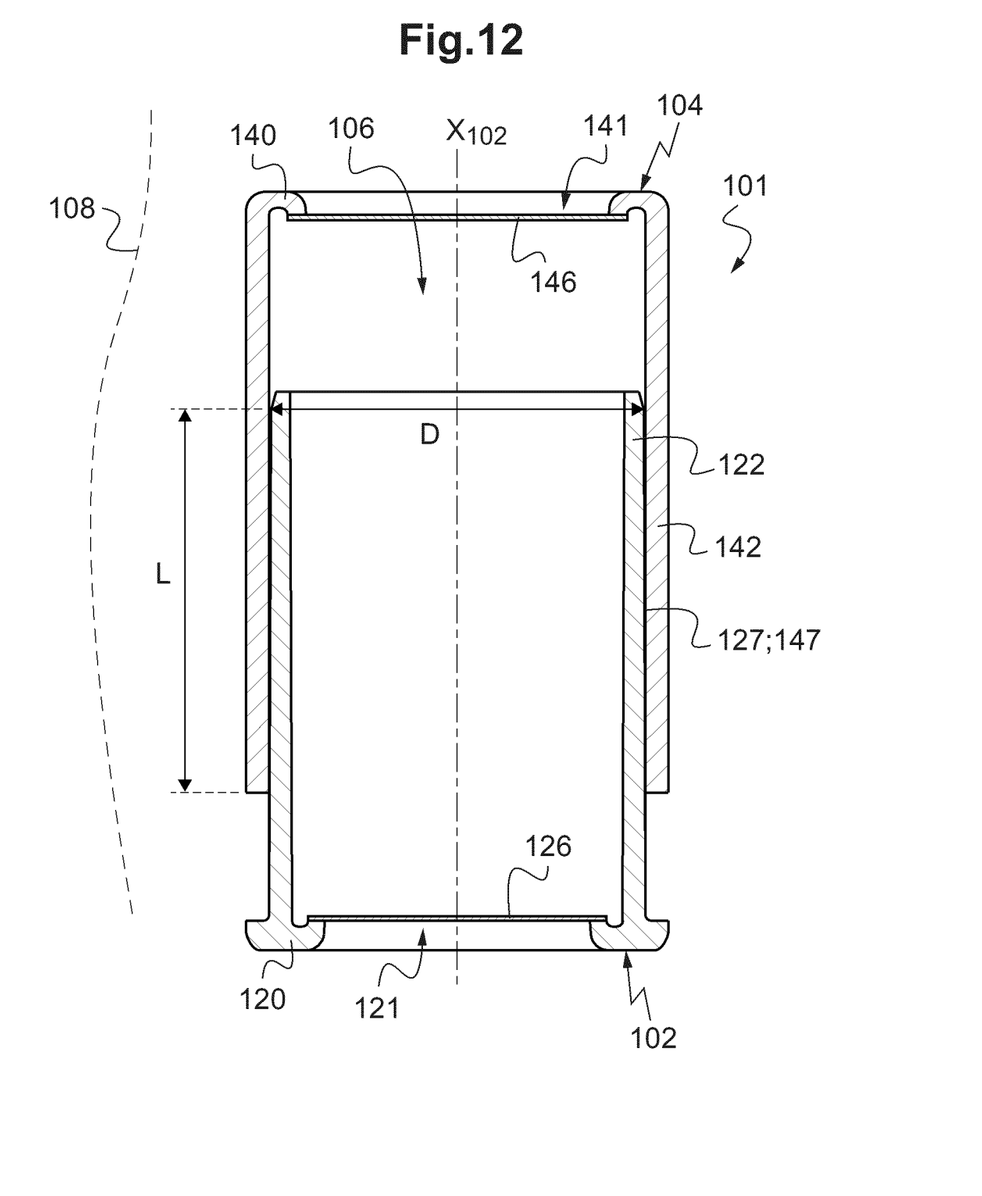
FIG. 12 is a longitudinal section of an assembly according to a second embodiment of the invention being a canister which comprises a tubular body and a cap delimiting a chamber for an active material.
Figure 13:
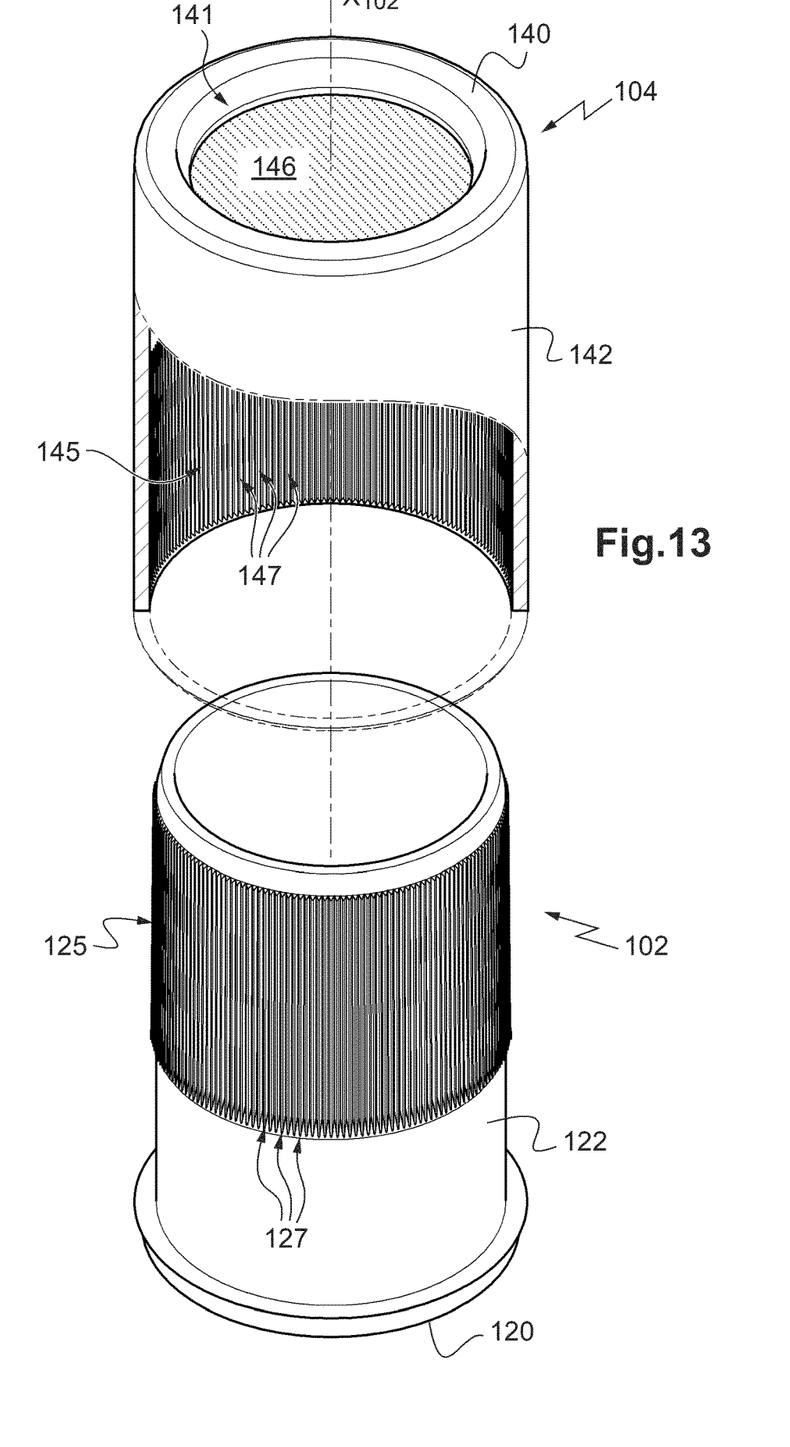
FIG. 13 is an exploded perspective view of the canister of FIG. 12.

In the second embodiment shown in FIGS. 12 and 13, elements that are similar to those of the first embodiment have the same references increased by 100. The assembly 1 of the second embodiment differs from the first embodiment in that it is a canister 101 formed by the association of a tubular body 102 and a cap 104. More precisely, the tubular body 102 and the cap 104 delimit therebetween a chamber 106 for an active material, where the chamber 106 advantageously has an adjustable volume. The canister 101 is intended to be dropped in a container 108 in which sensitive products are stored and regulate the atmosphere inside the container 108. The tubular body 102 has a circular cross section and comprises a transverse wall 120 and a peripheral wall 122. Similarly, the cap 104 has a tubular shape with a circular cross section and comprises a base wall 140 and a side wall 142. The transverse wall 120 of the tubular body and the base wall 140 of the cap each comprise a central hole 121, 141 which is covered with a porous membrane 126, 146 closing the respective hole 121, 141 so as to avoid escape of the active material out of the chamber 106. The membranes 126, 146 may be secured to the respective wall 120, 140 by any appropriate technique known in the art, e.g. by heat-sealing, ultrasonic welding, overmolding, etc.

For the attachment of the cap 104 relative to the tubular body 102, the side wall 142 of the cap 104 comprises on its inner periphery a plurality of longitudinal features in relief 147 configured to cooperate by mutual engagement with complementary longitudinal features in relief 127 provided on the outer surface of the peripheral wall 122 of the tubular body 102 substantially parallel to its longitudinal axis $X_{102}$. The longitudinal features in relief 127, 147 are contiguous to one another and form a striated surface 125, 145 all around the periphery of the corresponding part among the cap 104 and the tubular body 102. In the assembled configuration shown in FIG. 12, the longitudinal features in relief 147 of the cap 104 are engaged with the longitudinal features in relief 127 of the tubular body 102, so that the cap 104 is anchored relative to the tubular body 102 by surface interference, with the possibility of modulating the position of the cap relative to the tubular body and thus the volume of the chamber 106. In this second embodiment, the longitudinal features in relief 127, 147 have a shape with inclined flanks similar to that of the longitudinal features in relief 27, 47 of the first embodiment. Then, for each pair of complementary longitudinal features in relief 127, 147 in mutual engagement, the inclination of the cooperating flanks relative to the radial direction of the assembly ensures a tightening over a large surface of the complementary features in relief, which results in a strong anchoring of the cap 104 relative to the tubular body 102 by surface interference.

Figure 14:
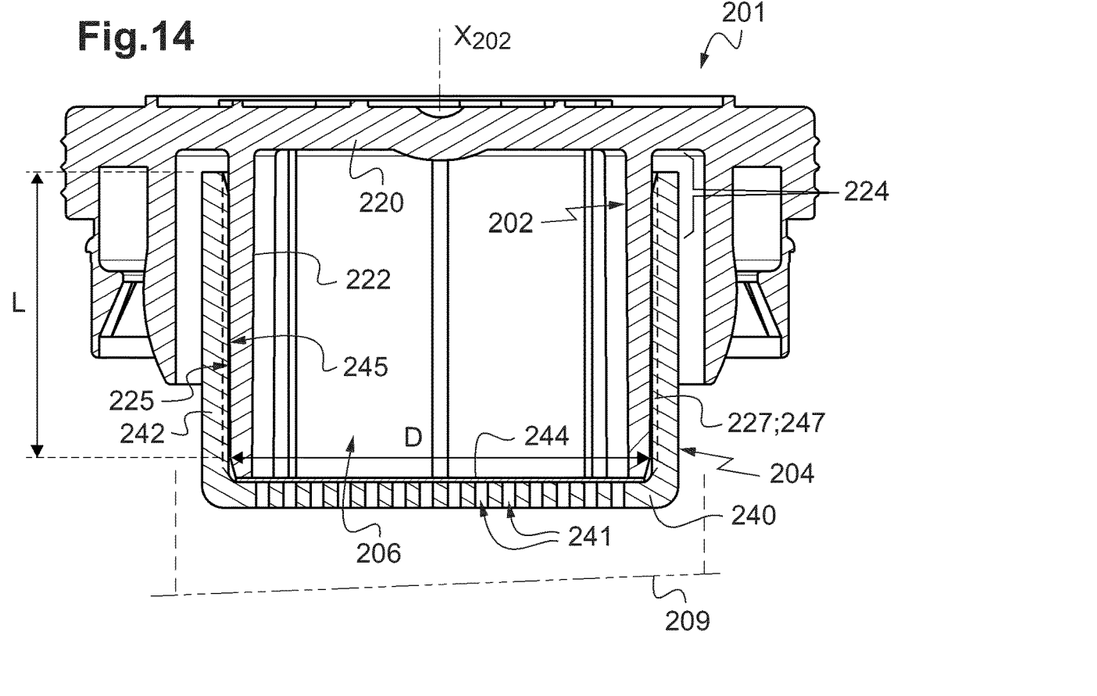
FIG. 14 is a longitudinal section of an assembly according to a third embodiment of the invention being a stopper which comprises a tubular body and a cap delimiting a chamber for an active material.
Figure 15:
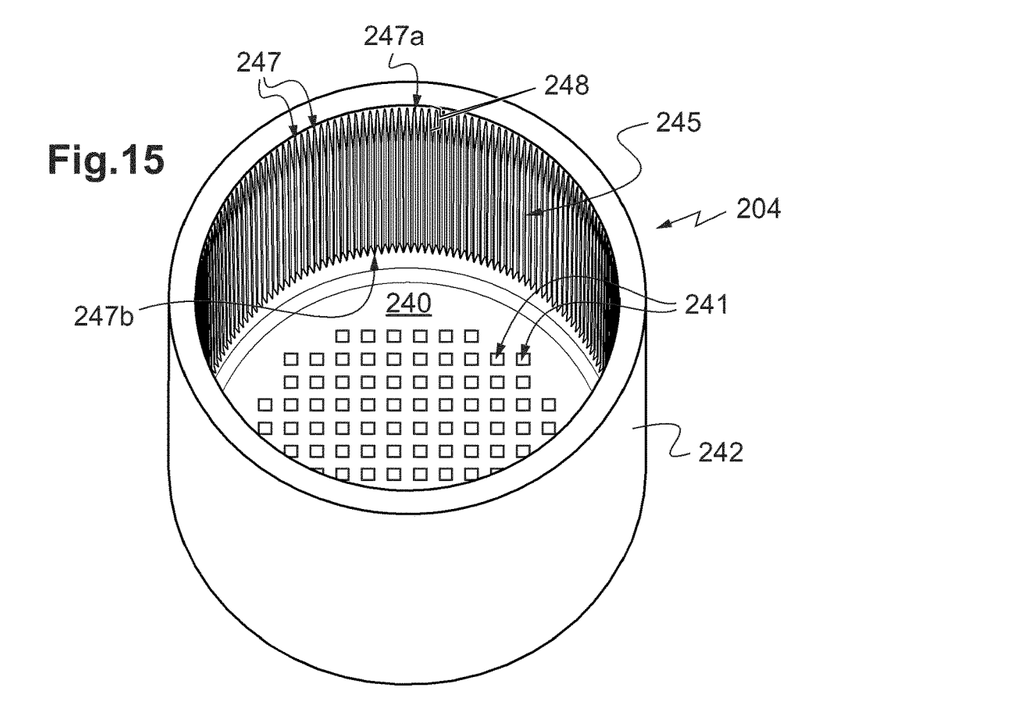
FIG. 15 is a perspective view of the cap of the stopper of FIG. 14.

In the third embodiment shown in FIGS. 14 and 15, elements that are similar to those of the first embodiment have the same references increased by 200. The assembly of the third embodiment differs from the first embodiment in that it is a stopper 201 formed by the association of a tubular body 202 and a cap 204 which delimit a chamber 206 for an active material within the stopper 201. The stopper 201 is configured to seal a container 209 in which sensitive products are stored, and additionally regulate the atmosphere inside the container 209. As in the previous embodiments, the tubular body 222 has a circular cross section and comprises a transverse wall 220 and a peripheral wall 222. Similarly, the cap 204 has a tubular shape with a circular cross section and comprises a base wall 240 and a side wall 242. The base wall 240 of the cap comprises a plurality of holes 241 which are covered with a cardboard 244 closing the holes 241 so as to avoid escape of the active material out of the chamber 206.

For the attachment of the cap 204 relative to the tubular body 202, the side wall 242 of the cap 204 comprises on its inner periphery a plurality of longitudinal features in relief 247 configured to cooperate by mutual engagement with complementary longitudinal features in relief 227 provided on the outer surface of the peripheral wall 222 of the tubular body 202 substantially parallel to its longitudinal axis $X_{202}$. Striated surfaces 225, 245 are thus formed all around the periphery of the corresponding part among the cap 204 and the tubular body 202. In the assembled configuration shown in FIG. 14, the longitudinal features in relief 247 of the cap 204 are engaged with the longitudinal features in relief 227 of the tubular body 202, so that the cap 204 is anchored relative to the tubular body 202 by surface interference. Here again, in this third embodiment, the longitudinal features in relief 227, 247 have a shape with inclined flanks similar to that of the longitudinal features in relief 27, 47 of the first embodiment, which ensures a tightening over a large surface of the complementary features in relief and results in a strong anchoring of the cap 204 relative to the tubular body 202 by surface interference.

The invention is not limited to the examples described and shown. In particular, in an assembly according to the invention, the cap and the tubular body may each comprise several striated surfaces distinct from one another and distributed around their periphery, instead of a striated surface formed all around their periphery. Other materials and shapes than those described above can also be considered for the constitutive elements of an assembly according to the invention.

The invention claimed is:

1. An assembly, such as a vial, a canister or a stopper, comprising a tubular body and a cap attached to the tubular body so as to form a chamber for an active material,
   wherein the tubular body comprises a transverse wall and a peripheral wall,
   wherein the cap comprises a base wall and a side wall, wherein the chamber is delimited by a part of the tubular body, including the transverse wall, and is closed by the cap,
   wherein the side wall of the cap comprises on its periphery a plurality of longitudinal features in relief which cooperate by mutual engagement with complementary longitudinal features in relief provided on the peripheral wall of the tubular body substantially parallel to its longitudinal axis,
   wherein at least one longitudinal feature in relief, of one among the cap and the tubular body, has two flanks inclined with respect to a radial direction of the cap or tubular body passing through the feature in relief, and wherein the cap is anchored relative to the tubular body by surface interference and, in the anchored configuration, both inclined flanks of the at least one longitudinal feature in relief of the one among the cap and the tubular body are in contact with a complementary longitudinal feature in relief of the other one among the cap and the tubular body.

2. The assembly of claim 1, wherein a plurality of longitudinal features in relief of one part among the cap and the tubular body, distributed circumferentially over the periphery of the part, have two flanks inclined with respect to a radial direction of the cap or tubular body passing through the considered feature in relief and, in the anchored configuration of the cap relative to the tubular body by surface interference, both inclined flanks of each longitudinal feature in relief having inclined flanks are in contact with a complementary longitudinal feature in relief of the other part among the cap and the tubular body.

3. The assembly of claim 1, wherein at least one longitudinal feature in relief of the cap has two flanks inclined with respect to a radial direction of the cap passing through the feature in relief, whereas at least one longitudinal feature in relief of the tubular body has two flanks inclined with respect to a radial direction of the tubular body passing through the feature in relief, wherein, in the anchored configuration of the cap relative to the tubular body by surface interference, the two inclined flanks of the at least one longitudinal feature in relief of the cap are in contact with the two inclined flanks of the at least one longitudinal feature in relief of the tubular body.

4. The assembly of claim 1, wherein the longitudinal features in relief of the tubular body, respectively the longitudinal features in relief of the cap, are contiguous to one another on the periphery of the tubular body, respectively on the periphery of the cap.

5. The assembly of claim 1, wherein the cap comprises on its periphery a plurality of longitudinal ribs, wherein each longitudinal rib has a rounded or chamfered (x) end portion at each end of the longitudinal rib which is configured to interact first with a complementary longitudinal groove of the tubular body upon mutual engagement of the cap and the tubular body.

6. The assembly of claim 1, wherein the length (L) over which the longitudinal features in relief cooperate by mutual engagement is higher than 1/10 of the diameter (D) of the tubular body.

7. The assembly of claim 1, wherein the successive longitudinal features in relief of the cap are distributed in a circumferential direction of the side wall with an angular pitch (B) between two successive features in relief of less than 3°.

8. The assembly of claim 1, wherein the cap comprises on its periphery a plurality of longitudinal ribs having a V-shaped cross section comprising an apex and two inclined flanks, whereas the tubular body comprises on its periphery a plurality of longitudinal grooves having a V-shaped cross section comprising a bottom and two inclined flanks.

9. The assembly of claim 8, wherein, for each longitudinal rib or longitudinal groove, the two flanks are inclined relative to each other at an angle (8) between 70° and 90°.

10. The assembly of claim 8, wherein, for each longitudinal rib of the cap, respectively for each longitudinal groove of the tubular body, the inclination angle of each flank relative to a radial direction passing through the apex of the rib, respectively through the bottom of the groove, is between 35° and 45°.

11. The assembly of claim 8, wherein the bottom of each longitudinal groove of the tubular body has a pointed shape, whereas the apex of each longitudinal rib of the cap has a rounded shape.

12. The assembly of claim 1, wherein the side wall of the cap and the peripheral wall of the tubular body each have a draft angle, wherein an absolute value of a difference between a draft angle (y) of the side wall of the cap and a draft angle (y') of the peripheral wall of the tubular body is less than 3°.

13. The assembly of claim 1, wherein the base wall of the cap comprises at least one hole covered with a gas-permeable protective sheet, such as a porous membrane, closing the hole.

14. The assembly of claim 1, wherein the assembly is a vial for storage of products, wherein the tubular body is a container inside which the cap delimits two compartments located on both sides of the cap, including a chamber for the active material on one side and a fillable tank on the other side.

15. The assembly of claim 14, wherein the side wall of the cap is a tubular wall having an open end on the opposite side from the base wall, wherein the cap is positioned in the container such that the open end faces away from the transverse wall of the container.

16. The assembly of claim 1, wherein the assembly is a canister comprising the chamber for the active material delimited between the tubular body and the cap, wherein the canister is configured to be dropped in a container and regulates an atmosphere inside the container.

17. The assembly of claim 1, wherein the assembly is a stopper inside which the tubular body and the cap delimit the chamber for the active material, wherein the stopper is configured to close a container and regulate an atmosphere inside the container.

18. The assembly of claim 1, wherein the chamber is filled with the active material selected from the group consisting of desiccants and an oxygen scavengers.

19. A method for manufacturing the assembly of claim 1, comprising
    filing a part of the tubular body, including the transverse wall, with the active material; and
    engaging longitudinal features in relief of the cap with complementary longitudinal features in relief of the tubular body until the base wall of the cap abuts the active material received in the tubular body.

20. The method of claim 19, wherein the cap is engaged relative to the tubular body by an actuator until a predetermined force applied on the cap by the actuator is reached or until a predetermined stroke of the actuator is reached, wherein the predetermined force, respectively the predetermined stroke, corresponds to a predefined level of compaction of the active material in the chamber.

* * * * *